(12) United States Patent
Huiku et al.

(10) Patent No.: US 10,092,226 B2
(45) Date of Patent: Oct. 9, 2018

(54) METHOD, ARRANGEMENT, SENSOR, AND COMPUTER PROGRAM PRODUCT FOR NON-INVASIVELY MEASURING HEMOGLOBIN CONCENTRATIONS IN BLOOD

(75) Inventors: Matti Huiku, Espoo (FI); Katja Urpalainen, Vantaa (FI)

(73) Assignee: General Electric Company, Schenectady, NY (US)

( * ) Notice: Subject to any disclaimer, the term of this patent is extended or adjusted under 35 U.S.C. 154(b) by 699 days.

(21) Appl. No.: 13/336,134

(22) Filed: Dec. 23, 2011

(65) Prior Publication Data

US 2013/0165757 A1 Jun. 27, 2013

(51) Int. Cl.
*A61B 5/1455* (2006.01)
*A61B 5/00* (2006.01)
*A61B 5/145* (2006.01)

(52) U.S. Cl.
CPC ...... *A61B 5/14551* (2013.01); *A61B 5/14535* (2013.01); *A61B 5/72* (2013.01)

(58) Field of Classification Search
CPC .............. A61B 5/1455; A61B 5/14551; A61B 5/14553
USPC .................................................. 600/310–344
See application file for complete search history.

(56) References Cited

U.S. PATENT DOCUMENTS

| | | | |
|---|---|---|---|
| 5,413,100 A | 5/1995 | Barthelemy et al. | |
| 5,729,333 A | 3/1998 | Osten et al. | |
| 5,830,133 A | 11/1998 | Osten et al. | |
| 6,104,938 A | 8/2000 | Huiku et al. | |
| 6,501,974 B2 | 12/2002 | Huiku | |
| 6,714,805 B2 | 3/2004 | Jeon et al. | |
| 7,884,933 B1 | 2/2011 | Kashyap et al. | |
| 2009/0024011 A1 | 1/2009 | Huiku | |

(Continued)

FOREIGN PATENT DOCUMENTS

| | | |
|---|---|---|
| CN | 1206339 A | 1/1999 |
| CN | 101438144 A | 5/2009 |
| JP | 3118446 A | 5/1991 |

(Continued)

OTHER PUBLICATIONS

Search Report and Written Opinion from corresponding PCT Application No. PCT/US2012/066176 dated Feb. 20, 2013.

(Continued)

*Primary Examiner* — Eric Winakur
*Assistant Examiner* — Marjan Fardanesh
(74) *Attorney, Agent, or Firm* — Andrus Intellectual Property Law, LLP

(57) ABSTRACT

A mechanism for non-invasively monitoring blood characteristics of a subject is disclosed. To enable measurement of hemoglobin concentrations in a cost-effective way, a computational model is established that represents a relationship between a first variable indicative of total hemoglobin concentration and a set of variables that includes second variables indicative of light transmission through tissue and third variables indicative of concentration percentages of different hemoglobin species. In-vivo measurement signals are acquired from a subject and in-vivo values are determined for the second and third variables based on the in-vivo measurement signals. The first variable is then solved based on the in-vivo values of the second and third variables and the computational model.

9 Claims, 3 Drawing Sheets

(56) References Cited

U.S. PATENT DOCUMENTS

2010/0076281 A1    3/2010   Navon

FOREIGN PATENT DOCUMENTS

| JP | 440940 A | 2/1992 |
| JP | 05228129 A | 9/1993 |
| JP | 06066633 U | 9/1994 |
| JP | 11104114 A | 4/1999 |
| JP | 2010522603 A | 7/2010 |
| WO | 2005083396 A1 | 9/2005 |
| WO | 2007/140422 A2 | 12/2007 |

OTHER PUBLICATIONS

Noiri et al., "Pulse total-hemoglobinonmeter provides accurate noninvasive monitoring", Crit Care Med 2005, vol. 33, No. 12.
Graaff, "Tissue Optics Applied to Reflectance Pulse Oximetry", University of Groningen, 1993, p. 188, ISBN 90-9006681-0.
Co-pending, nonpublished U.S. Appl. No. 13/076,662, filed Mar. 31, 2011, Huiku, "Calibration Method and Arrangement and Sensor for Non-Invasively Measuring Blood Chracteristics of a Subject".
Unofficial English Translation of Chinese Office Action and Search Report issued in connection with corresponding CN Application No. 2012800704526 dated Jul. 8, 2015.
Unofficial English Translation of Japanese Office Action and Search Report issued in connection with corresponding JP Application No. 2014549067 dated Nov. 1, 2016.

METHOD, ARRANGEMENT, SENSOR, AND COMPUTER PROGRAM PRODUCT FOR NON-INVASIVELY MEASURING HEMOGLOBIN CONCENTRATIONS IN BLOOD

BACKGROUND OF THE INVENTION

This disclosure relates to non-invasive determination of hemoglobin concentrations in blood, typically to non-invasive determination of total hemoglobin (THb) and hemoglobin fractions of a subject. This disclosure also relates to the apparatus, which is typically a pulse oximeter, and to a sensor and computer program product for the apparatus. Hemoglobin fractions here refer to the concentration percentages of different hemoglobin species.

Traditionally, hemoglobin measurements have been carried out based on in-vitro analysis of subject's blood. Measurement devices known as co-oximeters determine hemoglobin concentration from a blood sample by measuring spectral light transmission/absorption through a hemolysed blood sample at several wavelengths typically between 500 and 650 nm.

A major drawback related to co-oximeters is that the measurements are invasive, i.e. require a blood sample to be taken from the subject. Furthermore, the co-oximeters are rather expensive laboratory devices and require frequent service and maintenance.

One known technique for carrying out non-invasive in-vivo hemoglobin measurements is a so-called occlusion-release (OR) measuring technique, which is based on artificially induced changes in the blood flow of the patient. A typical OR based measurement device utilizes a ring-shaped cuff applied to the patient's finger. The device is further provided with a pressurizing arrangement to produce a state of temporary blood flow cessation in the finger by applying an over-systolic pressure and a state of transitional blood flow by releasing the over-systolic pressure. Measurement sessions are carried out during various states of blood flow and the blood absorption characteristics during the said states are analyzed to determine the concentration of a blood constituent, such as hemoglobin.

It is also known to combine the artificially induced changes in the blood flow with light transmission/absorption measurements at two or more wavelengths. These wavelengths typically include an isobestic wavelength (805 nm) and a wavelength at which water absorption is high (1310 nm or 1550 nm) to detect the concentrations of hemoglobin and water, respectively. It is also known to use the isobestic wavelength 805 urn and the water absorbing wavelength 1250 nm for measuring the total hemoglobin concentration using cardiac pulsating signals alone. Oxy-, deoxy-, carboxy- and methemoglobin fractions can be solved simultaneously with the total hemoglobin concentration using one set of equations and a total of six wavelengths.

Compared to invasive techniques, non-invasive optical hemoglobin or hematocrit measurements have clear advantages, which include the elimination of both painful blood sampling and the risk of infection. Furthermore, non-invasive measurements are simpler to carry out and require less training of the nursing staff.

However, there are also several drawbacks related to the above non-invasive techniques, as described below.

First, the devices that are based on stopping all or part of the blood flow are rather complicated since the optical measurement involves synchronized operation of the optical and pneumatic components of the measurement device.

Second, these measurements cannot be carried continuously, but a certain measurement period is required for each measurement. Typically, the measurement cycle is manually initiated, which makes the devices suitable for spot checks after the need for the hemoglobin measurement has been recognized based on symptoms of the subject/patient. Consequently, these non-invasive hemoglobin meters cannot be used for alarming of a sudden hemoglobin or blood loss.

Third, normal low-cost silicon detectors, which are used in standard pulse oximeters, can be used only in the visible and near infrared region, since their response ends at a wavelength of about 1100 nm. Therefore, more expensive detector technology, e.g, InGaAs detectors, must be used for enabling measurement of water absorption in the short-wavelength infrared region, such as at wavelengths around 1200-1300 nm. Coupled with the more expensive infrared emitters in this wavelength range, this need increases the cost of the sensor to many fold compared to silicon technology emitter and detector sensors.

Fourth, the measurements of total hemoglobin concentration and all hemoglobin fractions, including oxy-, deoxy-, carboxy- and methemoglobin percentages, require the use of two detectors as one detector cannot cover all wavelengths, from about 600 nm to about 1300 nm, required for the simultaneous measurement. Typically, a silicon detector is still needed for accurate carboxyhemoglobin reading, since carboxyhemoglobin absorbs light only below 700 nm, where a standard InGaAs detector cannot be used.

A hemoglobin measurement method is also known in which a theoretical relationship is formed, which is indicative of the effect of tissue on in-vivo measurement signals at the wavelengths of the apparatus. Hemoglobin concentration may be determined based on the theoretical relationship by requiring that the effect of the in-vivo tissue on the in-vivo signals is consistent for all wavelengths at which the in-vivo measurement is performed. This involves using a tissue model that includes hemoglobin concentration as one of the parameters, and adjusting the hemoglobin concentration in the model until consistency is reached. As the final result is to be searched for through iteration, this is actually a rather indirect measurement method and the result may still depend on other tissue parameters. Therefore, it would be desirable to obtain a more straightforward mechanism that eliminates the above drawbacks. It would also be desirable to be able to use the same wavelength set of the sensor for calculating both total hemoglobin and the hemoglobin fractions in blood, thereby to obtain a complete picture of the blood composition non-invasively and continuously with a compact and low-cost solution.

BRIEF DESCRIPTION OF THE INVENTION

The above-mentioned problems are addressed herein which will be comprehended from the following specification.

To enable measurement of hemoglobin concentrations in a cost-effective way, the device is provided with a computational model that defines a variable indicative of total hemoglobin concentration through a model that includes hemoglobin fractions as variables of the model. The model may be constructed so that the measured absorption includes the contribution of scattering in the total absorption. Due to these features, a complete picture of blood composition may be obtained through a single set of measurement signals at wavelengths below about 1100 nm, i.e. with a single low-cost detector.

In an embodiment, a method for non-invasively measuring hemoglobin concentrations in blood comprises establishing a computational model representing a relationship between a first variable indicative of total hemoglobin concentration and a set of variables that includes second variables indicative of light transmission through tissue and third variables indicative of concentration percentages of different hemoglobin species. The method further comprises acquiring in-vivo measurement signals from a subject, determining, based on the in-vivo measurement signals, in-vivo values for the second and third variables, and solving the first variable based on the in-vivo values of the second and third variables and the computational model.

In another embodiment, an apparatus or arrangement for non-invasively measuring hemoglobin concentrations in blood comprises a computational model representing a relationship between a first variable indicative of total hemoglobin concentration and a set of variables that includes second variables indicative of light transmission through tissue and third variables indicative of concentration percentages of different hemoglobin species. The arrangement further comprises a first calculation unit configured to determine, based on in-vivo measurement signals obtained from a subject, in-vivo values for the second and third variables and a second calculation unit configured to solve the first variable based on the in-vivo values of the second and third variables and the computational model.

In a still further embodiment, a computer program product for non-invasively measuring hemoglobin concentrations in blood comprises a first program product portion adapted to receive a computational model representing a relationship between a first variable indicative of total hemoglobin concentration and a set of variables that includes second variables indicative of light transmission through tissue and third variables indicative of concentration percentages of different hemoglobin species. The computer program product further comprises a second program product portion adapted to determine, based on in-vivo measurement signals obtained from a subject, in-vivo values for the second and third variables and a third program product portion adapted to solve the first variable based on the in-vivo values of the second and third variables and the computational model.

Various other features, objects, and advantages of the invention will be made apparent to those skilled in the art from the following detailed description and accompanying drawings.

DETAILED DESCRIPTION OF THE INVENTION

A pulse oximeter comprises a computerized measuring unit and a sensor or probe attached to the subject, typically to finger or ear lobe of the subject. The sensor includes at least one light source for sending optical signals through the tissue and at least one photo detector for receiving the signal transmitted through or reflected from the tissue. On the basis of the transmitted and received signals, light absorption by the tissue may be determined. During each cardiac cycle, light absorption by the tissue varies cyclically. During the diastolic phase, absorption is caused by venous blood, non-pulsating arterial blood, cells and fluids in tissue, bone, and pigments, whereas during the systolic phase there is an increase in absorption, which is caused by the inflow of arterial blood into the tissue part on which the sensor of the pulse oximeter is attached. Pulse oximeters focus the measurement on this pulsating arterial blood portion by determining the difference between the peak absorption during the systolic phase and the background absorption during the diastolic phase. Pulse oximetry is thus based on the assumption that the pulsatile component of the absorption is due to arterial blood only.

In order to distinguish between two species of hemoglobin, oxyhemoglobin ($HbO_2$), and deoxyhemoglobin (RHb), absorption must be measured at two different wavelengths, i.e. the sensor of a traditional pulse oximeter includes two different light sources, such as LEDs or lasers. The wavelength values widely used are 660 nm (red) and 940 nm (infrared), since the said two species of hemoglobin have substantially different absorption at these wavelengths. Each light source is illuminated in turn at a frequency which is typically several hundred Hz.

Figure 1:
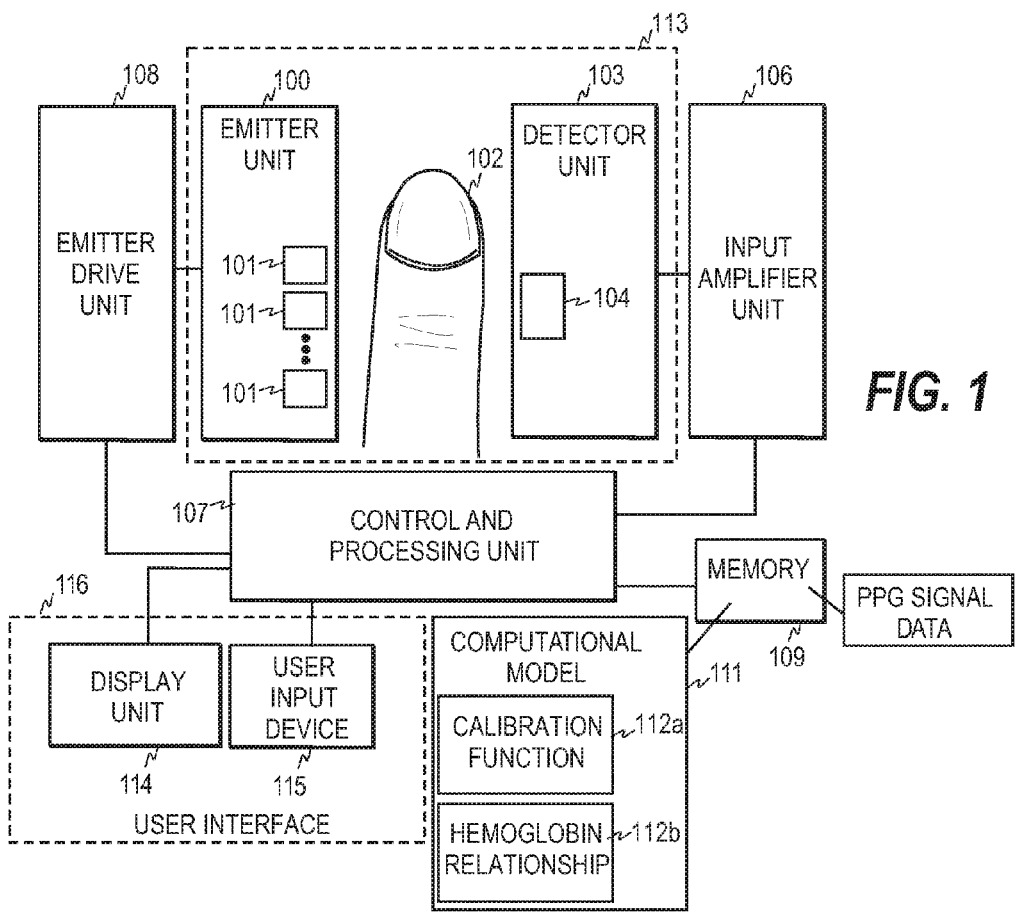
FIG. 1 is a block diagram illustrating one embodiment of a multi-wavelength pulse oximeter.

FIG. 1 is a block diagram of one embodiment of a multi-wavelength pulse oximeter. Light transmitted from an emitter unit 100 passes into patient tissue, such as a finger 102. The emitter unit includes multiple light sources 101, such as LEDs, each light source having a dedicated wavelength. Each wavelength forms one measurement channel on which photoplethysmographic waveform data is acquired. In the embodiments of the disclosed apparatus, the number of sources/wavelengths is at least three, typically four to ten, and all wavelengths may be in the sub-micron range, i.e. below about 1100 nm. That is, the water absorption needs not to be measured.

The light propagated through or reflected from the tissue is received by a detector unit 103, which comprises one photo detector 104 in this example. The emitter and detector units form the sensor 113 of the pulse oximeter.

The photo detector converts the received optical signals into electrical pulse trains and feeds them to an input amplifier unit 106. The amplified measurement channel signals are further supplied to a control and processing unit 107, which converts the signals into digitized format for each wavelength channel.

The control and processing unit further controls an emitter drive unit 108 to alternately activate the light sources. As mentioned above, each light source is typically illuminated several hundred times per second. With each light source being illuminated at such a high rate compared to the pulse rate of the patient, the control and processing unit obtains a high number of samples at each wavelength for each cardiac cycle of the patient. The value of these samples varies according to the cardiac cycle of the patient, the variation being caused by the arterial blood.

The digitized photoplethysmographic (PPG) signal data at each wavelength may be stored in a memory 109 of the control and processing unit before being processed further by the calculation algorithms of the control and processing unit.

For the determination of hemoglobin characteristics, such as hemoglobin fractions and total hemoglobin (THb), the control and processing unit is adapted to execute one or more calculation algorithms, which may be stored in the memory of the control and processing unit. The obtained concentrations are shown on the screen of a display unit 114 of a user interface 116, which also includes a user input device 115. The calculation algorithm(s) establishe(s) a computational model 111 that represents a (mathematical) relationship between in-vivo measurement signals obtained from the subject and the desired hemoglobin characteristics, such as the concentration of total hemoglobin (THb) and hemoglobin fractions. In one embodiment, the algorithm(s) may comprise two logical entities: a model 112a that models an intermediate variable using the measured data and a relationship 112b that relates the intermediate variable to the total hemoglobin. The model 112a serves as a calibration function that defines the intermediate variable as a function of parameters measurable from a subject. In a further embodiment the relationship 112b can be omitted, in which case the computational model may be a regression model that directly models total hemoglobin using measured signals, hemoglobin fractions, and other tissue parameters as independent variables of the model. The data for the computational model may be stored in the memory before the pulse oximeter is taken into use, as is discussed below. The operations carried out prior to the actual use of the pulse oximeter are in this context referred to as off-line operations, while the actual in-vivo measurements are referred as on-line operations.

As is known, the so-called Lambert-Beer law expresses how light is absorbed by matter. According to the Lambert-Beer law, the intensity of an incident light beam drops exponentially as it passes through an absorbing sample. Here, the term functional light transmittance (FLT) is used to refer to the fraction of incident light that passes through the sample: $FLT_i = I/I_0$, wherein $I_0$ is the intensity of the incident light, I is the intensity of the light passed through the sample, and i is the wavelength of the light. According to the Lambert-Beer law, $FLT_i = I/I_0 = e^{-\alpha x}$, where α is effective attenuation coefficient and x is the path length.

Figure 2:
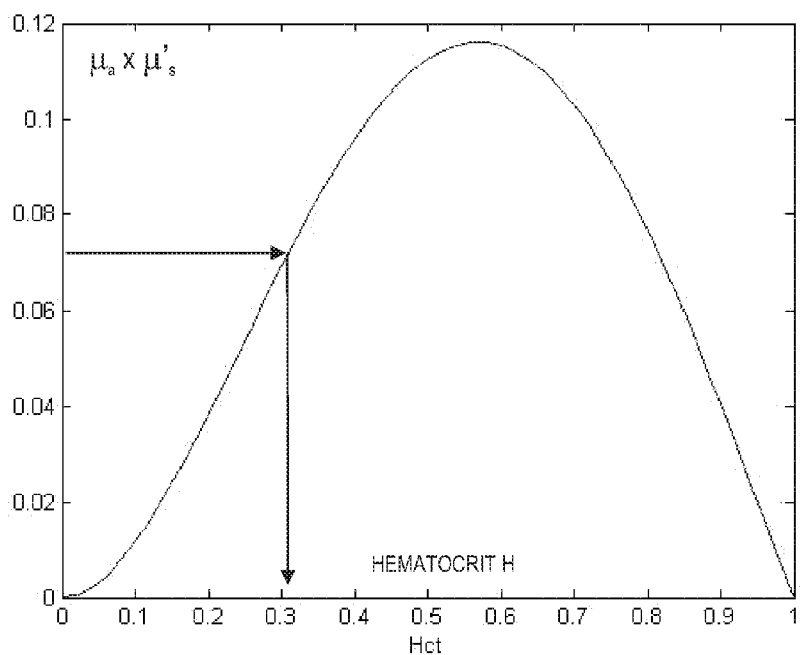
FIG. 2 illustrates the empirical relationship between an intermediate variable and hematocrit found in red blood cell suspensions.
Figure 3:
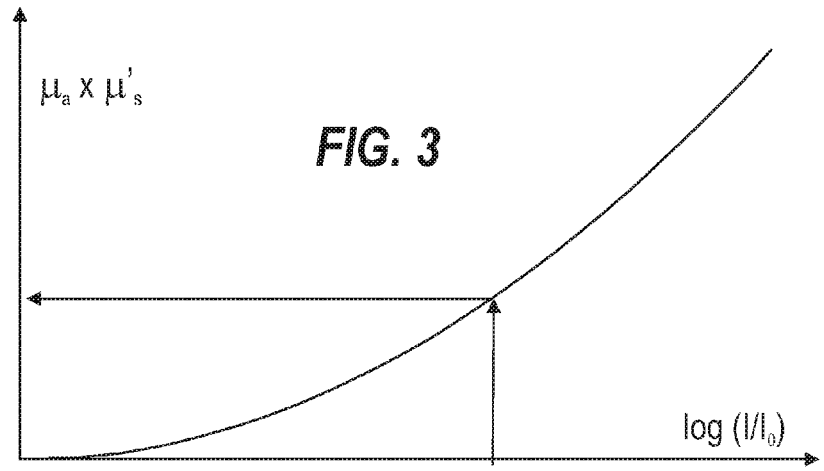
FIG. 3 illustrates a relationship between the intermediate variable and effective attenuation coefficient of tissue.

In an embodiment of the disclosed measurement method, the above-mentioned intermediate parameter is determined through a model that uses independent variables indicative of the DC component of the light transmission/absorption. FIGS. 2 and 3 illustrate the basic steps of the method in terms of determination of hemoglobin concentration. Hemoglobin determination is based on a relationship empirically verified in red blood cell (RBC) suspensions (R. Graaff, Tissue Optics Applied to Reflectance Pulse Oximetry, Groningen: University of Groningen, 1993, p. 188, ISBN 90-9006681-0). In RBC suspension, the scattering of a single cell is influenced by the presence of neighboring cells. Reduced scattering coefficient per unit volume of suspension $\mu_s'$ is described in the literature as a function of hematocrit Hct by the equation: $\mu_s' = \sigma_s / V_{ery} \times Hct \times (1-Hct) \times (1.4-Hct)$, where Hct is the hematocrit, i.e. the volume fraction of the red blood cells, $\sigma_s$ the reduced scattering coefficient of a single RBC, and $V_{ery}$ the volume of a single RBC. On the other hand, absorption coefficient $\mu_a$ per unit volume in RBC suspension is directly proportional to the hematocrit, and may be written as $\mu_a = \sigma_a / V_{ery} \times Hct$, where $\sigma_a$ is the absorption coefficient of a single red blood cell. The product $\mu_a \times \mu_s'$ is thus represented by the equation $\mu_a \times \mu_s' = (\sigma_a \times \sigma_s / V^2_{ery}) \times Hct \times Hct \times (1-Hct) \times (1.4-Hct) = c_{cell} \times Hct \times Hct \times (1-Hct) \times (1.4-Hct)$, (Eq. 1), where $c_{cell}$ describes the absorbtion and scattering efficiencies of one cell. This relationship between hematocrit and the product $\mu_a \times \mu_s'$ is presented in FIG. 2. The product $\mu_a \times \mu_s'$ is here used as the above-mentioned intermediate variable through which the hemoglobin concentration may be determined. The intermediate variable has a first part ($\sigma_a$ or $\mu_a$) that carries within itself a signature of the spectral absorption of the hemoglobin confined to blood and a second part, $Hct \times Hct \times (1-Hct) \times (1.4-Hct)$, that is indicative of the density of the red blood cells in the RBC suspension. Due to this, the measured absorption takes into account the contribution of scattering in the total light attenuation through tissue.

As mentioned above, light transmission through a tissue layer of thickness x is described by $I = I_0 \times e^{-\alpha x}$, (Eq. 2), where $I_0$ is the incoming light intensity and α is the effective attenuation coefficient for the tissue layer. By solving the light transport equation using a so-called diffusion approximation gives for the effective attenuation coefficient:

$$\alpha^2 = 3 \times \mu_a \times (\mu_a + \mu_s'),\qquad\text{(Eq. 3)}.$$

Because in red blood cell suspension $\mu_a \ll \mu_s'$, the effective attenuation coefficient for the RBC suspension can be approximated simply by $$\alpha^2 = 3 \times \mu_a \times \mu_s'.\qquad\text{(Eq. 4)}.$$

In real tissues, blood is the dominating absorber and, therefore, the contribution of tissues other than blood to the total absorption of in-vivo tissues is low. The transmission through real tissue, such as a finger, is thus determined by the blood in tissue plus the attenuation effect in the medium that scatter the light beam away from the light source-detector line. The scattering efficiency of bloodless tissues is smaller than scattering in blood, and because, in addition, absorption in bloodless tissue is very small, the overall contribution to the effective attenuation coefficient by tissue remains small. Under these assumptions the light transmission through a living tissue reflects well the properties of blood, and, therefore $\alpha^2 = 3 \times \mu_a \times \mu_s' \sim [\log(I/I_0)]^2 / x^2 \sim [\log(I/I_0)]^2$, (Eq. 5) where $\mu_a$ is the absorption coefficient and $a_s'$ the scattering coefficient in whole blood. That is, the effective attenuation coefficient of a tissue layer is proportional to $\log(FLT_i)$, i.e. to the logarithm of the fraction of total light transmission through tissue. This relationship between $\log(I/I_0)$ and the intermediate variable $\mu_s \times \mu_s'$ is illustrated in FIG. 3.

In one embodiment of the measurement method, an empirical relationship is first established between measured light transmissions and the effective attenuation in blood using Eq. 5. The relationship may be used to determine the intermediate variable $\mu_a \times \mu_s'$. Then Eq. 1 (FIG. 2) may be used to determine hematocrit based on the intermediate variable. The calibration of the apparatus serves as a transformation that transfers the calculation to an ideal whole blood cuvette environment in which a relationship exists between the intermediate variable and the desired hemoglobin characteristics. Thus, the calibration data stored in the apparatus may be used to transform the in-vivo signals/variables to a variable of the theoretical domain within which the desired hemoglobin characteristics can be derived from the said variable.

The relationship illustrated in FIG. 3 may be established by employing measured tissue transmissions $FLT(\lambda) = I(\lambda)/I_0(\lambda)$ at all wavelengths X used in the pulse oximeter sensor. In one embodiment, the relationship between the intermediate variable $\mu_a \times \mu_s'$ and the actual light transmissions is found by linear regression using $\log(FLT(\lambda))$ and $[\log(FLT(\lambda))]^2$ as independent variables of the regression model. Therefore, instead that strictly obeying the theory above, the terms log(FLT($\lambda$)) may be maintained in the regression model in order to account for deviations from the above simple theory. As the intermediate variable $\mu_s \times \mu_s'$ is wavelength dependent, different estimates for the variable $\mu_s \times \mu_s'$ may be obtained. The estimate obtained at each wavelength may be converted to correspond to the variable $\mu_a \times \mu_s'$ at a certain reference wavelength, preferably the isobestic wavelength of oxy- and deoxyhemoglobin (805 nm). When the composition of the hemoglobin species, oxy-, deoxy-, carboxy-, and methemoglobin, is known, the conversion means that, first, the total $\mu_a$ at each wavelength is determined as the weighted sum of the absorption coefficients $\mu_a^{HbXj}$ of the hemoglobin species $HbX_j$, the weights being the relative concentrations of the hemoglobin species. That is, $\mu_a(\lambda) = HbO2 \times \mu_a^{HbO2}(\lambda) + RHb \times \mu_a^{RHb}(\lambda) + HbMet \times \mu_a^{HbMet}(\lambda) + HbCO \times \mu_a^{HbCO}(\lambda)$ where HbO2, RHb, HbMet, and HbCO are the concentration percentages of oxyhemoglobin, deoxyhemoglobin, methemoglobin, and carboxyhemoglobin, respectively.

Then, the same total $\mu_a(\lambda^{REF})$ is determined for the reference wavelength $\lambda^{REF}$. The ratio between the reference wavelength absorption and each of the other wavelength absorptions determines the conversion factor $F(\lambda)$, and $\mu_a(\lambda^{REF}) = F(\lambda) \times \mu_a(\lambda)$. Similarly, the scattering efficiency at a wavelength $\lambda$ can be converted to correspond to the scattering efficiency at a reference wavelength $\lambda^{REF}$ by using the known Mie theory approximation (R. Graaff, Tissue Optics Applied to Reflectance Pulse Oximetry, Groningen: University of Groningen, 1993, p. 188, ISBN 90-9006681-0) for the scattering coefficient $\mu_s' \approx \sigma_s = 3.28 \times \pi \times a^2 \times z^{0.37} \times (m-1)^{2.09} = constant \times \lambda^{-0.37}$, where the red blood cells are approximated as spheres with a radius a and refraction index m; $z = 2 \times \pi \times a / \lambda$. This results in a second conversion factor $G(\lambda) = (\lambda / \lambda^{REF})^{0.37}$. The total conversion factor for the $\mu_a \times \mu_s'$ is thus $F(\lambda) \times G(\lambda)$. In other words, the variable $\mu_a \times \mu_s'$ at the reference wavelength $\lambda^{REF}$ equals $F(\lambda) \times G(\lambda)$ times the variable $\mu_a \times \mu_s'$ at wavelength $\lambda$.

To calibrate the pulse oximeter, blood samples are drawn from subjects, and the hematocrit value Hct and the concentration fractions $HbX_j$, are determined and used further to determine, using the relationship of FIG. 2, the value of the intermediate variable $\mu_a \times \mu_s'$ at the reference wavelength.

Using the above different estimates, $\mu_a(\lambda^{REF}) \times \mu_s'(\lambda^{REF})$ obtained for the intermediate variable at the reference wavelength, a conclusive estimate $<\mu_a \times \mu_s'>$ may then be formed, for instance, by averaging all different estimates. This value is then related to the simultaneously measured light transmissions, or actually to their logarithms. Consequently, the calibration process results in a relationship $$<\mu_a \times \mu_s'> = f_1(\log(FLT(\mu_i)), [\log(FLT(\lambda_i)]^2, HbX_j, \phi_i),$$
$$i = 1 \ldots N, \quad (Eq. 6)$$

where f is the calibration function that may be obtained by linear regression, FLTs are the light transmissions, $HbX_j$ represents the hemoglobin fractions, and $\phi_i$ symbolizes potential other independent parameters at wavelength $k_i$ that are needed for compensating various tissue effects, such as skin color.

Figure 4:
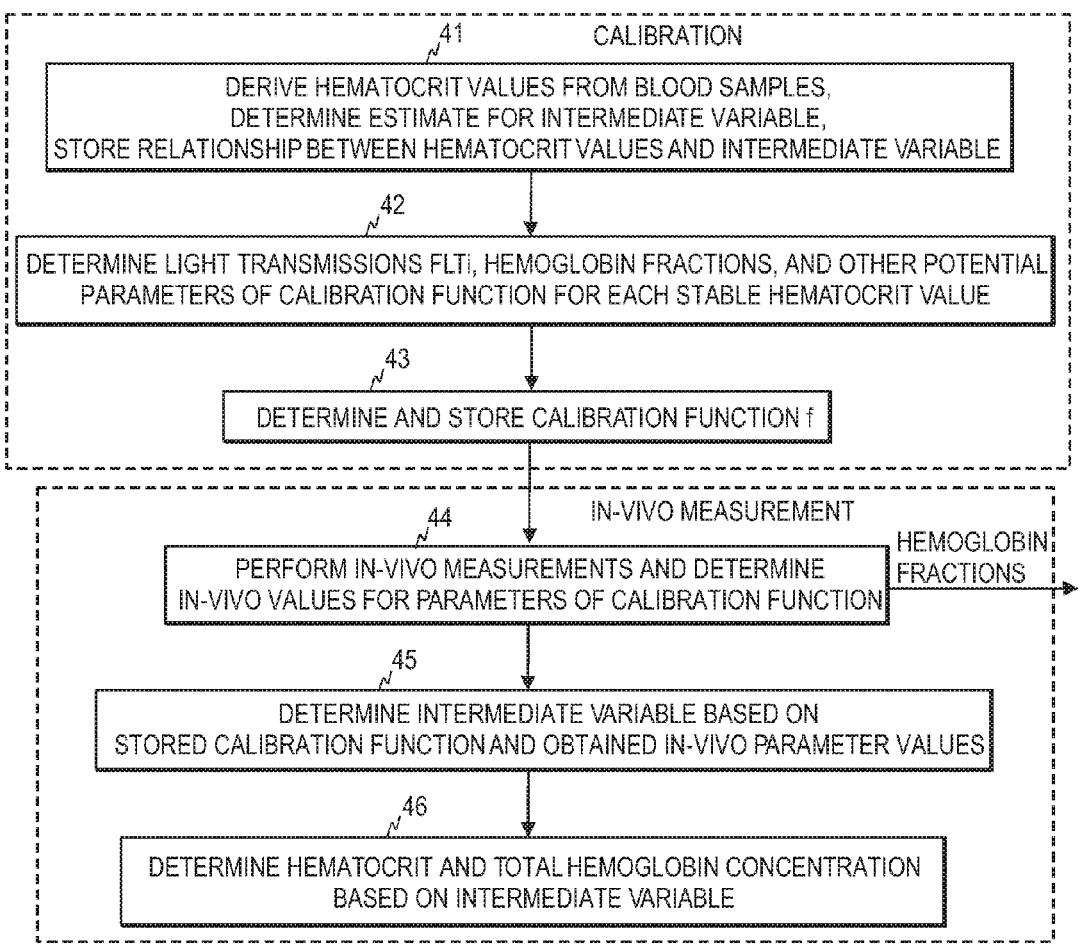
FIG. 4 is a flow diagram illustrating one embodiment of determination of hemoglobin characteristics of a subject.

FIG. 4 illustrates the steps carried out in one embodiment of the method to obtain blood characteristics of a subject. First, the off-line operations are carried out in steps 41 to 43 to calibrate the pulse oximeter. In step 41, a wide range of hematocrit Hct values may be determined from blood samples taken at stable Hct levels and a conclusive estimate may be determined for the intermediate variable, as is described above. Thus, in step 41 the relationship according to FIG. 2 is generated for the pulse oximeter, so that the hematocrit value may be determined based on the obtained intermediate variable in subsequent in-vivo measurements. This relationship is stored in the memory of the pulse oximeter in step 41.

In step 42, the parameters/variables (FLTi, $HbX_j$, $\phi_i$) needed for the calibration function f may be determined for each stable Hct in the above range of hematocrit values. The parameters/variables and the values of the conclusive estimate of the intermediate variable at each level of Hct are then used in step 43 to find the calibration function f (Eq. 6) for the pulse oximeter. This calibration function is stored in the pulse oximetry memory. Thus, in steps 42 and 43 a calibration function according to Eq. 6 is defined as described above and stored in the pulse oximeter. The calibration function may be a regression model that models the dependent variable (intermediate variable) by using known mathematical methods.

Steps 41 to 43, which form the calibration of the apparatus, are typically carried out in the manufacturing phase of the apparatus, after which the apparatus is ready for continuous monitoring of hemoglobin concentration.

When the pulse oximeter is taken into use, on-line measurements are performed to obtain in-vivo measurement signals from a subject. Based on the in-vivo measurement signals, parameters of the calibration function, i.e. independent variables of the regression model, are determined (step 44). As discussed above, these independent variables may include hemoglobin fractions $HbX_j$. The fractions may be determined by using transformations adapted to transform the in-vivo measured differential absorption signals, $dA_k^{in-vivo} = (AC/DC)_k$, at wavelength k, to corresponding non-scatter signals $dA_k^{LB}$ according to the Lambert-Beer model. In a typical transformation-based pulse oximeter, the measured in-vivo signals are first transformed into signals applicable to the Lambert-Beer model and then a linear set of equations applicable in the Lambert-Beer model is solved to obtain the fractional concentrations of different hemoglobin species. Mathematically the operation of a transformation-based pulse oximeter may be expressed as follows: $dA_i^{LB} = g(dA_k^{in-vivo}, p_k)$, in which $dA_i^{LB}$ is a fictitious Lambert-Beer model signal at wavelength i, $dA_k^{in-vivo}$ is the measured in-vivo signal at wavelength k (k=1 ... M, in which M is the number of wavelengths), g is a transformation function describing statistically the photon path lengths in the tissue, and $P_k$ refers to one or more tissue property variables indicative of absorption and scattering characteristics of the subject's tissue. The differential absorption signal according to the Lambert-Beer model can be written for four different hemoglobin species $HbX_j$ (deoxyhemoglobin, oxyhemoglobin, carboxyhemoglobin, and methemoglobin) and for eight wavelengths as follows:

$$\begin{pmatrix} dA_1 \\ \vdots \\ dA_8 \end{pmatrix}^{LB} = c \times \begin{pmatrix} \varepsilon_1^{RHb} & \varepsilon_1^{HbO2} & \varepsilon_1^{HbCO} & \varepsilon_1^{HbMet} \\ \vdots & \vdots & \vdots & \vdots \\ \vdots & \vdots & \vdots & \vdots \\ \varepsilon_8^{RHb} & \varepsilon_8^{HbO2} & \varepsilon_8^{HbCO} & \varepsilon_8^{HbMet} \end{pmatrix} \times \begin{pmatrix} RHb \\ HbO2 \\ HbCO \\ HbMet \end{pmatrix} \quad (Eq.8)$$

in which HbO2, RHb, HbMet, and HbCO are the concentrations of oxyhemoglobin, deoxyhemoglobin, methemoglobin, and carboxyhemoglobin, respectively, the $\varepsilon$ matrix is for the extinction coefficients of the four different hemoglobin species at the eight wavelengths, and c is a constant. When there are more than four wavelengths and thereby more than four measured signals and still only four unknown hemoglobin concentrations, the concentration fractions must be solved, for instance, in the least square sense: $c \times (HbX_j) = (\varepsilon_{ij}^T \varepsilon_{ij})^{-1} (\varepsilon_{ij}^T \times (dA_i^{LB}))$, where the $\varepsilon_{ij}^T$ is the transpose of the extinction matrix $\varepsilon_{ij}$, $i=1 \ldots M$, and $j=1 \ldots 4$, in which $M>4$ is the number of wavelengths. Finally, the constant c is determined so that the concentration fractions sum up to 100%.

An estimate of the intermediate variable $\mu_a \times \mu_s'$ may then be determined in step 45 based on the stored calibration function and the obtained parameters. Finally, hematocrit may be determined in step 46 using Eq. 1 stored in the pulse oximeter in step 41. The total hemoglobin concentration corresponding to the measured hematocrit value can be optionally calculated using the relation $THb = 330$ g/l$\times$Hct, where Hct is the obtained hematocrit value. As the total hemoglobin is known, the hemoglobin fraction percentages obtained in step 44 may now be supplemented by deriving absolute fraction values from the percentages and the total hemoglobin value. Oxygen content in arterial blood may further be determined based on the absolute oxyhemoglobin values.

The differential absorption signal $dA^{LB}$ itself (Eq. 8) is another example of an intermediate variable that is defined in an ideal non-scatter LB blood cuvette. It has a first part, $\varepsilon \times HbX_j$ that carries within itself a signature of the hemoglobin absorption. The constant c is the second part, which is proportional to the total hemoglobin concentration and the pulsating blood volume, $c = THb \times d1$, in which d1 is the pulsed optical path length in the LB blood cuvette.

In the above embodiment, a regression model for the $dA^{LB}$ is developed by keeping the measured differential absorptions $dA^{in\text{-}vivo}$ and the measured hemoglobin fractions $HbX_j$ as independent variables. Mathematically this regression model may be written as $dA_i^{LB} = f_2(dA_k^{in\text{-}vivo}, HbX_j, P_k)$, in which the additional parameters $P_k$ describe the confounding tissue effects and $f_2$ is the calibration function (and k refers to wavelength k). The regression model is developed to a normalized LB optical path length and, therefore, signals $dA^{LB}$ can directly give the total hemoglobin THb. In fact, this embodiment may be regarded as equivalent to a direct regression model of THb using the measured signals, the hemoglobin concentration fractions and possible tissue parameters as the independent variables of the model: $THb = f_3(dA_k^{in\text{-}vivo}, HbX_j, P_P)$, where $f_3$ is the calibration function.

In a further combined embodiment, both $\mu_a \times \mu_s'$ and dA may be employed as independent variables of the regression model modeling total hemoglobin: $THb = f_4(\log(FLT_k), dA_k^{in\text{-}vivo}, HbX_j, P_k)$, where $f_4$ is the calibration function. In this embodiment the independent variables can be in linear or quadratic form, and cross-terms may also be included. Thus, model variables indicative of light transmission through tissue may include both variables representing logarithms of the fraction of total light transmission through tissue (log(FLT)) and variables representing pulsating light transmission through tissue ($dA^{in\text{-}vivo}$).

Figure 5:
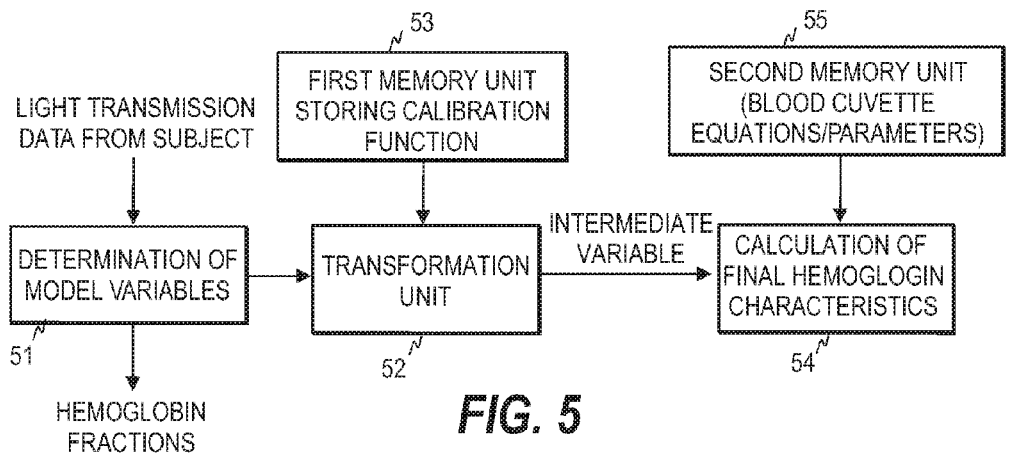
FIG. 5 illustrates an example of the operational entities of a processing unit of a pulse oximeter.

In terms of the on-line calculation process, the functionalities of the control and processing unit 107 may be divided into the operational units shown in FIG. 5. A variable determination unit 51 is configured to determine the values of the regression model variables based on the measured in-vivo signals. As the hemoglobin fractions belong to the regression model variables, this unit outputs the in-vivo hemoglobin fractions. A transformation unit 52 is configured to carry out the transformation from the in-vivo domain to the blood cuvette domain where the intermediate variable is applicable. For this, the transformation unit uses the calibration function, i.e. the model coefficients stored in a first memory unit 53 of the device prior to the commissioning of the device. A calculation unit 54 is further configured to calculate the final hemoglobin characteristics, hematocrit or THb, based on the intermediate variable output from the transformation unit. For this, the calculation unit uses the relationships stored in a second memory unit 55 of the device prior to the commissioning of the device. It is to be noted that FIG. 5 illustrates the division of the functionalities of the control and processing unit in logical sense and in terms of the determination of hemoglobin concentrations. In a real apparatus the functionalities may be distributed in different ways between the elements or units of the apparatus or system. Since the computational model may also be constructed without the intermediate variable, the functionalities may also be divided at general level so that unit 51 forms a first calculation unit adapted to determine the in-vivo values of the model variables, including hemoglobin fractions, while the other units form a second calculation unit adapted to use the said variables to solve the final hemoglobin characteristics, i.e. hematocrit and possibly also total hemoglobin.

The above-described solution enables both total hemoglobin and hemoglobin fraction measurements in a single sensor or apparatus that uses low cost, high power silicon emitters, and a low cost silicon photodiode detector, i.e. the more expensive detector technology necessary in the short-wavelength infrared region is not required. The wavelength range covered is typically 600-1000 nm, which also means that the water amount in blood is not measured directly.

Since the concentration measurement rests on a conventional $SpO_2$ measurement, the only instrument needed is a pulse oximeter employing multiple, at least three, wavelengths. Furthermore, any additional hardware, such as an arrangement for controlling the blood flow of the subject, is not required. The measurement is also easy to perform and may be carried out continuously, and the straightforward algorithm enables a complete picture of blood composition to be obtained with reduced computing power. The measurement and apparatus is thus suitable to diagnostics and monitoring of hemoglobin concentrations at various locations, such as hospitals, doctor's offices and homes inasmuch as the solution allows automatic and continuous evaluation of blood composition to be introduced in clinical set-ups and in self-care devices in a cost-effective way.

Figure 6:
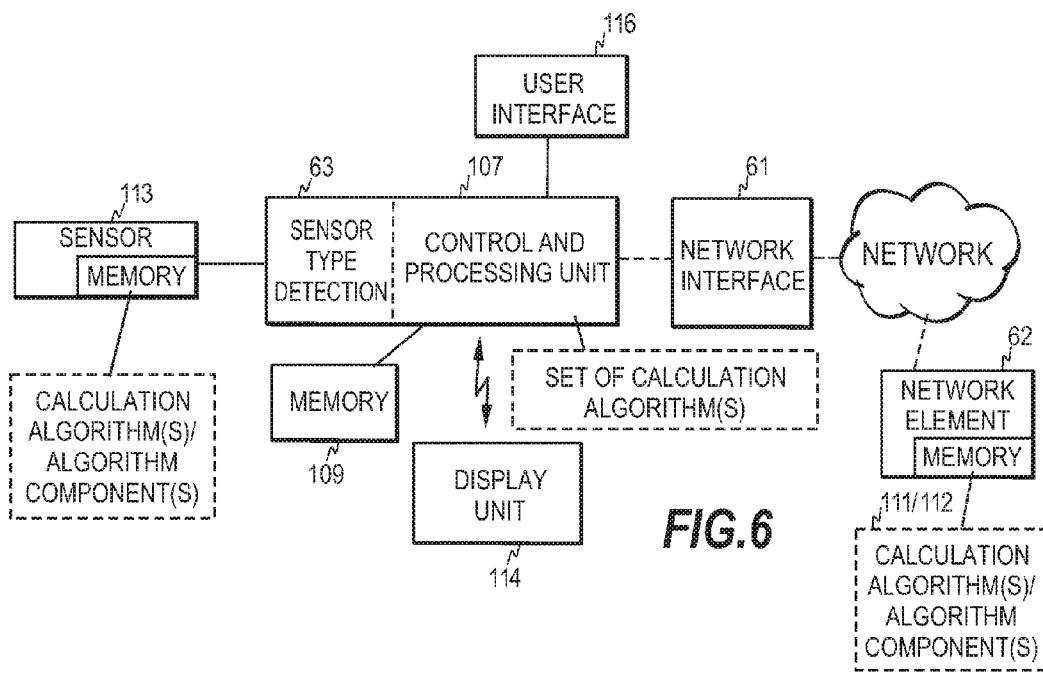
FIG. 6 illustrates an example of a pulse oximeter system.

The pulse oximeter of FIG. 1 includes, in addition to the normal $SpO_2$ algorithm, hemoglobin calculation algorithm(s) that may be stored in the memory of the pulse oximeter in the manufacturing phase of the apparatus. As discussed above, the calculation algorithm(s) form the computational model that describes the relationship between the desired hemoglobin characteristics (THb and/or Hct) and in-vivo signals/parameters. However, it is to be noted that the elements of the computational model, i.e. variables and equations, are not necessarily stored in the actual pulse oximeter or in its control and processing unit, but the elements of the computational model may be distributed between the sensor attached to the subject, the actual pulse oximeter device, i.e. the control and processing unit, and/or a communication network. Thus, a complete pulse oximeter may be realized as a compact or distributed device. Below, the term arrangement is used to refer to the multiple possible device implementations in this respect. FIG. 6 illustrates an example of an arrangement in which the control and processing unit 107 is provided with a network interface 61 for downloading/updating the computational model or components thereof through a network from a network element 62 storing the model or components thereof, such as updated coefficients. This is illustrated with dotted lines in the figure. The calculation algorithm(s) 112 or the components thereof may also be stored in the sensor 113, as is illustrated in FIG. 6. The control and processing unit may also hold different calculation algorithms for different sensor types. The sensors may be provided with an identifier identifying the calculation algorithm(s) that may be used with the sensor. In one embodiment of the arrangement, the control and processing unit is compatible with both a conventional sensor (two wavelengths) and an advanced sensor employing the above-described calculation algorithm(s). The control and processing unit 107 may be provided with a recognition module 63 for recognizing the type of the sensor and reading the model identifier. If the recognition module detects that an advanced sensor is connected to it, it may download data from the sensor and/or network according to the blood characteristics to be determined and displayed. The user of the device may select the data to be displayed through the user interface 116.

A pulse oximeter may also be upgraded to a device capable of determining the concentration of a substance in the blood of a subject. Such an upgrade may be implemented by delivering to the pulse oximeter a software module that enables the device to carry out the above steps. The software module may be delivered, for example, on a data carrier, such as a CD or a memory card, or through a telecommunications network. The software module may be provided with the calculation algorithm(s) or components thereof and/or with operational entities adapted to access an external memory holding the algorithm(s) or algorithm components, such as regression model coefficients. The software module may comprise three portions: a first portion adapted to receive the computational model, a second portion adapted to determine, based on in-vivo measurement signals obtained from a subject, the in-vivo values for the model variables (such as hemoglobin fractions), and a third portion adapted to solve the THb (or hematocrit) based on the in-vivo values of the model variables and the computational model.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for non-invasively measuring hemoglobin concentrations in blood of a subject, the method comprising
establishing a pre-determined first relationship between a first variable indicative of total hemoglobin concentration and an intermediate variable, wherein the first relationship is based on blood samples from at least one other subject and the intermediate variable represents a product of absorption coefficient $\mu_a$ per unit and reduced scattering coefficient $\mu_s'$ per unit volume;
determining a second relationship between the intermediate variable and a set of variables that includes second variables indicative of light transmission through tissue and third variables indicative of concentration percentages of different hemoglobin species;
storing the first and second relationships in a memory;
acquiring in-vivo measurement signals from the subject using a sensor of a pulse oximeter that includes an emitter and a detector performing measurements of at least three wavelengths;
determining, based on the in-vivo measurement signals from the subject, in-vivo values for the second and third variables;
determining the intermediate variable based on the second relationship;
solving for the first variable based on the pre-determined first relationship between the intermediate variable and the first variable; and
determining the hemoglobin concentrations based on the first variable and displaying the hemoglobin concentrations on a display unit.

2. The method according to claim 1, wherein the second variables are logarithms indicative of total light transmission through the tissue.

3. The method according to claim 1, wherein the second variables are indicative of pulsating light transmission through the tissue.

4. The method according to claim 1, wherein the acquiring includes acquiring the in-vivo measurement signals at wavelengths below about 1100 nm.

5. An arrangement for non-invasively measuring hemoglobin concentrations in blood of a subject, the arrangement comprising:
a pulse oximeter including at least one sensor having an emitter and a detector operable to obtain in vivo measurement signals of at least three wavelengths from the subject;
a control unit including a memory device including a stored pre-determined first relationship between a first variable indicative of total hemoglobin concentration and an intermediate variable and a second relationship between the intermediate variable and a set of variables that includes second variables indicative of light transmission through tissue and third variables indicative of concentration percentages of different hemoglobin species, wherein the pre-determined first relationship is determined based on blood samples from at least other subject and the intermediate variable represents a product of absorption coefficient $\mu_a$ per unit and reduced scattering coefficient $\mu_s'$ per unit volume;
a first calculation unit configured to determine, based on the in-vivo measurement signals obtained from the subject, in-vivo values for the second and third variables;
a second calculation unit configured to solve the first variable based on the in-vivo values of the second and third variables and the stored first and second relationships; and
a display unit to display the hemoglobin concentrations.

6. The arrangement according to claim 5, wherein the second variables are logarithms indicative of total light transmission through the tissue.

7. The arrangement according to claim 5, wherein the second variables are indicative of pulsating light transmission through the tissue.

8. The arrangement according to claim 5, wherein the in-vivo measurement signals are at wavelengths below about 1100 nm.

9. A non-transitory computer-readable medium for use with a computer processor for non-invasively measuring hemoglobin concentrations in blood of a subject, the non-transitory computer-readable medium comprising:

a first program product portion including a pre-determined first relationship determined based on blood samples from at least one other subject, the pre-determined first relationship representing a relationship between a first variable indicative of total hemoglobin concentration and an intermediate variable and a second relationship between the intermediate variable and a set of variables that includes second variables indicative of light transmission through tissue and third variables indicative of concentration percentages of different hemoglobin species, wherein the intermediate variable represents a product of absorption coefficient $\mu_a$ per unit and reduced scattering coefficient $\mu_s'$ per unit volume;

a second program product portion adapted to determine, based on in-vivo measurement signals obtained from a sensor having an emitter and a detector performing measurements of at least three wavelengths configured to be positioned on the subject, in-vivo values for the second and third variables; and a third program product portion adapted to solve the first variable based on the in-vivo values of the second and third variables and the first and second relationships.

\* \* \* \* \*